US012370365B2

(12) United States Patent
Haddock et al.

(10) Patent No.: US 12,370,365 B2
(45) Date of Patent: Jul. 29, 2025

(54) SYSTEMS FOR NOISE-SENSITIVE PATIENT-SPECIFIC ADJUSTMENTS OF NEUROMODULATION PARAMETERS

(71) Applicant: Boston Scientific Neuromodulation Corporation, Valencia, CA (US)

(72) Inventors: Andrew James Haddock, Los Angeles, CA (US); Rosana Esteller, Santa Clarita, CA (US); Michael A Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 612 days.

(21) Appl. No.: 17/634,011

(22) PCT Filed: Aug. 6, 2020

(86) PCT No.: PCT/US2020/045240
§ 371 (c)(1),
(2) Date: Feb. 9, 2022

(87) PCT Pub. No.: WO2021/030152
PCT Pub. Date: Feb. 18, 2021

(65) Prior Publication Data
US 2022/0339447 A1    Oct. 27, 2022

Related U.S. Application Data

(60) Provisional application No. 62/885,027, filed on Aug. 9, 2019.

(51) Int. Cl.
*A61N 1/36* (2006.01)
(52) U.S. Cl.
CPC ..... *A61N 1/36139* (2013.01); *A61N 1/36062* (2017.08); *A61N 1/36132* (2013.01)

(58) Field of Classification Search
CPC ............ A61N 1/36139; A61N 1/36132; A61N 1/36062; A61N 1/37252
See application file for complete search history.

(56) References Cited

U.S. PATENT DOCUMENTS

| 7,136,695 B2 | 11/2006 | Pless et al. |
| 10,569,088 B2 * | 2/2020 | Dinsmoor .......... A61N 1/36062 |

(Continued)

FOREIGN PATENT DOCUMENTS

| AU | 2020327928 B2 | 7/2023 |
| EP | 4010065 B1 | 10/2023 |
| WO | WO-2021030152 A1 | 2/2021 |

OTHER PUBLICATIONS

"International Application Serial No. PCT/US2020/045240, International Search Report mailed Nov. 11, 2020", 6 pgs.

(Continued)

*Primary Examiner* — Tammie K Marlen
(74) *Attorney, Agent, or Firm* — Schwegman Lundberg & Woessner, P.A.

(57) ABSTRACT

An example method for delivering neurostimulation energy may include performing a training procedure by delivering the neurostimulation energy to a neural target of the patient when the patient is at one or more postures. Electrical activity is sensed from the spinal cord, such as an electrospinogram (ESG). A relationship is determined between the sensed electrical activity and neurostimulation intensity that reduces influence of noise in the sensed electrical activity caused by dynamically changing posture of the patient using mathematical or statistical modeling of the extracted features. Stimulation parameters are modulated according to the determined relationship.

20 Claims, 13 Drawing Sheets

(56) References Cited

U.S. PATENT DOCUMENTS

| | | |
|---|---|---|
| 2006/0253166 A1 | 11/2006 | Flaherty et al. |
| 2010/0114198 A1 | 5/2010 | Donofrio et al. |
| 2010/0114202 A1 | 5/2010 | Donofrio et al. |
| 2010/0114208 A1 | 5/2010 | Donofrio et al. |
| 2015/0032181 A1 | 1/2015 | Baynham et al. |
| 2019/0070418 A1* | 3/2019 | Hincapie Ordonez ................... A61N 1/36135 |
| 2019/0209844 A1 | 7/2019 | Esteller et al. |

OTHER PUBLICATIONS

"International Application Serial No. PCT/US2020/045240, Written Opinion mailed Nov. 11, 2020", 7 pgs.

"Australian Application Serial No. 2020327928, First Examination Report mailed Dec. 8, 2022", 3 pgs.

"Australian Application Serial No. 2020327928, Response filed Feb. 28, 23 to First Examination Report mailed Dec. 8, 2022", 19 pgs.

"European Application Serial No. 20761026.2, Response to Communication pursuant to Rules 161 and 162 filed Jul. 20, 2022", 6 pgs.

"International Application Serial No. PCT/US2020/045240, International Preliminary Report on Patentability mailed Feb. 17, 2022", 9 pgs.

\* cited by examiner

SYSTEMS FOR NOISE-SENSITIVE PATIENT-SPECIFIC ADJUSTMENTS OF NEUROMODULATION PARAMETERS

CLAIM OF PRIORITY

This application is a U.S. National Stage Filing under 35 U.S.C. 371 from International Application No. PCT/US2020/045240, filed Aug. 6, 2020 and published in English as WO 2021/030152 on Feb. 18, 2021, which claims the benefit of priority under 35 U.S.C. § 119 (c) of U.S. Provisional Patent Application Ser. No. 62/885,027, filed on Aug. 9, 2019, each of which is herein incorporated by reference in its entirety.

TECHNICAL FIELD

This document relates generally to neuromodulation and more particularly to methods for noise-sensitive patient-specific adjustments of stimulation parameters for neuromodulation using sensed electrical activity.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES).

Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

SCS, by way of example and not limitation, has been used to treat chronic pain syndromes. A change in posture of a patient receiving SCS may cause a change in thickness of cerebrospinal fluid between the one or more electrodes and the target site, which may impact effectiveness of the SCS or cause a patient to experience discomfort.

SUMMARY

An example (e.g. "Example 1") of a system for delivering neurostimulation energy through a plurality of electrodes may include a stimulation control circuit configured to deliver the neurostimulation energy at one or more neurostimulation intensity levels to a neural target at or near a spinal cord of the patient when the patient is at one or more postures. The system may further include a sensing input configured to sense electrical activity from the spinal cord, the electrical activity including responses to the delivered neurostimulation energy. The system may also include a feature extraction module configured to extract features from the sensed electrical activity when the patient is at the one or more postures. The system may further include a training module configured to determine a relationship between the sensed electrical activity and neurostimulation intensity that reduces influence of noise in the sensed electrical activity caused by dynamically changing posture of the patient using mathematical or statistical modeling of the extracted features. The stimulation control circuit may be configured to modulate stimulation parameters according to the determined relationship.

In Example 2, the subject matter of Example 1 may optionally be configured such that the sensing input is configured to receive an electrospinogram (ESG).

In Example 3, the subject matter of any one or any combination of Examples 1-2 may optionally be configured such that the mathematical modeling includes using a dynamical model incorporating one or more of a Kalman filter (KF) or a Hidden Markov Model (HMM).

In Example 4, the subject matter of any one or any combination of Examples 1-3 may optionally be configured such that the mathematical modeling includes using a risk-sensitive control strategy based on a selection of risk parameters specific for the patient.

In Example 5, the subject matter of Example 4 may optionally be configured such that the selection of risk parameters includes an indication of pain or discomfort tolerance of the patient.

In Example 6, the subject matter of any one or any combination of Examples 1-5 may optionally be configured such that the training module is configured for re-training to determine an adjusted relationship between posture of the patient and the intensity of neurostimulation energy that reduces influence of noise in the received ESG.

In Example 7, the subject matter of Example 6 may optionally be configured such that the re-training is configured to be automatically triggered.

In Example 8, the subject matter of Example 6 may optionally be configured such that the re-training is configured to be requested by the patient.

In Example 9, the subject matter of any one or any combination of Examples 6-8 may optionally be configured such that the re-training uses stimulation parameters identified by the training module or a clinician.

In Example 10, the subject matter of any one or any combination of Examples 6-8 may optionally be configured such that the re-training uses stimulation parameters provided by the patient using a remote control.

In Example 11, the subject matter of any one or any combination of Examples 6-10 may optionally be configured such that the re-training includes an application configured to execute on a mobile electronic device configured to wirelessly communicate with an implantable pulse generator (IPG) of the patient.

In Example 12, the subject matter of any one or any combination of Examples 1-11 may optionally be configured such that the determination of the relationship is configured to have a duration of less than one minute.

In Example 13, the subject matter of any one or any combination of Examples 1-12 may optionally be configured such that the one or more neurostimulation intensity levels includes a discomfort threshold of the patient.

In Example 14, the subject matter of any one or any combination of Examples 1-12 may optionally be configured such that the one or more neurostimulation intensity levels includes a perception threshold of the patient.

In Example 15, the subject matter of any one or any combination of Examples 1-12 may optionally be configured such that the one or more neurostimulation intensity levels includes a therapeutic threshold of the patient.

An example (e.g. "Example 16") of a method for delivering neurostimulation energy through a plurality of electrodes to a patient having a spinal cord may include performing a training procedure by delivering the neurostimulation energy at one or more neurostimulation intensity levels to a neural target of the patient when the patient is at one or more postures. The method may further include sensing electrical activity from the spinal cord, the electrical activity including the delivered neurostimulation energy. The method may also include determining a relationship between the sensed electrical activity and neurostimulation intensity that reduces influence of noise in the sensed electrical activity caused by dynamically changing posture of the patient using mathematical or statistical modeling of the extracted features. The method may further include modulating stimulation parameters according to the determined relationship.

In Example 17, the subject matter of Example 16 may optionally be configured such that sensing the electrical activity includes using an electrospinogram (ESG).

In Example 18, the subject matter of any one or any combination of Examples 16-17 may optionally be configured such that the mathematical modeling includes using a dynamical model incorporating one or more of a Kalman filter (KF) or a Hidden Markov Model (HMM).

In Example 19, the subject matter of any one or any combination of Examples 16-18 may optionally be configured such that the mathematical modeling includes using a risk-sensitive control strategy based on a selection of risk parameters specific for the patient.

In Example 20, the subject matter of Example 19 may optionally be configured such that the selection of risk parameters includes an indication of pain or discomfort tolerance of the patient.

In Example 21, the subject matter of Example 16 may optionally be configured such that the mathematical modeling includes using a probabilistic model implementing a neural network or other statistical models and a dynamical model incorporating one or more of a Kalman filter (KF) or a Hidden Markov Model (HMM).

In Example 22, the subject matter of Example 16 may optionally be configured such that the mathematical modeling includes using a probabilistic model implementing a neural network or other statistical models and a risk-sensitive control strategy based on a selection of risk parameters specific for the patient.

In Example 23, the subject matter of Example 16 may optionally be configured such that the mathematical modeling includes using a dynamical model incorporating one or more of a Kalman filter (KF) or a Hidden Markov Model (HMM) and a risk-sensitive control strategy based on a selection of risk parameters specific for the patient.

In Example 24, the subject matter of Example 16 may optionally be configured such that the mathematical modeling includes using a probabilistic model implementing a neural network or other statistical model, a dynamical model incorporating one or more of a Kalman filter (KF) or a Hidden Markov Model (HMM), and a risk-sensitive control strategy based on a selection of risk parameters specific for the patient.

In Example 25, the subject matter of Example 24 may optionally be configured such that the selection of risk parameters includes an indication of a discomfort threshold of the patient.

An example (e.g. "Example 26") of a non-transitory machine-readable medium including instructions, which when executed by a machine, cause the machine to perform a method for delivering neurostimulation energy through a plurality of electrodes to a patient having a spinal cord, and the method may include performing a training procedure by delivering the neurostimulation energy at one or more neurostimulation intensity levels to a neural target of the patient when the patient is at one or more postures. The method may further include sensing electrical activity from the spinal cord, the electrical activity including the delivered neurostimulation energy. The method may also include determining a relationship between the sensed electrical activity and neurostimulation intensity that reduces influence of noise in the sensed electrical activity caused by dynamically changing posture of the patient using mathematical or statistical modeling of the extracted features. The method may further include modulating stimulation parameters according to the determined relationship.

In Example 27, the subject matter of Example 26 may optionally be configured such that sensing the electrical activity includes using an electrospinogram (ESG).

In Example 28, the subject matter of any one or any combination of Examples 26-27 may optionally be configured such that the one or more neurostimulation intensity levels includes a discomfort threshold of the patient.

In Example 29, the subject matter of any one or any combination of Examples 26-28 may optionally be configured such that the one or more neurostimulation intensity levels includes a perception threshold of the patient.

In Example 30, the subject matter of any one or any combination of Examples 26-29 may optionally be configured such that the one or more neurostimulation intensity levels includes a therapeutic threshold of the patient.

An example (e.g. "Example 31") of a system for delivering neurostimulation energy through a plurality of electrodes may include an implantable pulse generator (IPG) configured for spinal neurostimulation therapy, one or more leads configured to connect the IPG to the plurality of electrodes, and a stimulation control circuit. The stimulation control circuit may be configured to deliver the neurostimulation energy using the plurality of electrodes at one or more neurostimulation intensity levels to a neural target at or near a spinal cord of the patient when the patient is at one or more postures. The system may also include a sensing input configured to sense electrical activity from the spinal cord, the electrical activity including responses to the delivered neurostimulation energy. The system may further include a feature extraction module configured to extract features from the sensed electrical activity when the patient is at the one or more postures. The system may also include a training module configured to determine a relationship between the sensed electrical activity and neurostimulation intensity that reduces influence of noise in the sensed electrical activity caused by dynamically changing posture of the patient using mathematical or statistical modeling of the extracted features. The stimulation control circuit may be further configured to modulate stimulation parameters according to the determined relationship.

In Example 32, the subject matter of Example 31 may optionally be configured such that the sensing input is configured to receive an electrospinogram (ESG).

In Example 33, the subject matter of any one or any combination of Examples 31-32 may optionally be configured such that the mathematical modeling includes using a dynamical model incorporating one or more of a Kalman filter (KF) or a Hidden Markov Model (HMM).

In Example 34, the subject matter of any one or any combination of Examples 31-33 may optionally be configured such that the mathematical modeling includes using a risk-sensitive control strategy based on a selection of risk parameters specific for the patient.

In Example 35, the subject matter of Example 34 may optionally be configured such that the selection of risk parameters includes an indication of pain or discomfort tolerance of the patient.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to the use of sensed electrical activity, such as ESG, to make noise-sensitive patient-specific adjustments of stimulation parameters for SCS neuromodulation. This document provides an overview of an SCS system, and then a discussion of using sensed electrical activity with such an SCS system to dynamically compensate for postural changes of a patient.

Figure 1:
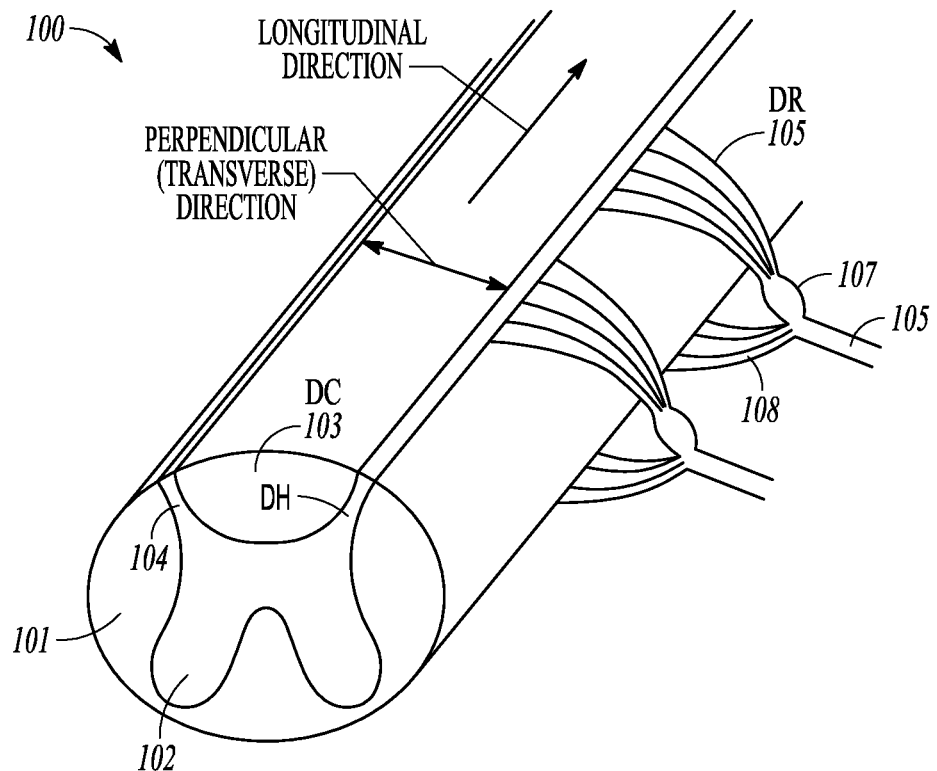
FIG. 1 illustrates, by way of example, a portion of a spinal cord.

Various embodiments described herein involve spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been conventionally targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). The present subject matter may be implemented with sub-perception therapy and may be implemented with therapy that is perceivable.

Sub-perception therapy may include higher frequency modulation (e.g. about 1000 Hz or above) of the spinal cord that effectively blocks the transmission of pain signals in the afferent fibers in the DC. Some embodiments may implement this higher frequency modulation may include 1200 Hz or above, and some embodiments may implement this higher frequency modulation may include 1500 Hz or above. Some embodiments use waveforms with lower frequencies (e.g. less than 1200 Hz) to provide sub-perception therapy. Some embodiments provide sub-perception modulation of DC tissue to provide a sub-perception therapy without paresthesia. Some embodiments herein selectively modulate DH tissue, such as the presynaptic terminals of pain inhibitory neurons in the spinal cord, over DC tissue. Some embodiments selectively stimulate DR tissue and/or dorsal root ganglion over DC tissue to provide sub-perception therapy.

Selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle. The selected modulation may be delivered with fixed widths. Although the target filed can be applied any pulse width that the device is capable of delivering, longer pulses widths are believed to be more effective.

Figure 2:
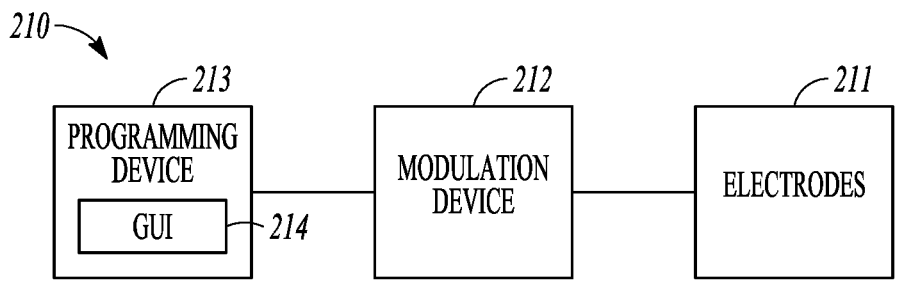
FIG. 2 illustrates, by way of example, an embodiment of a neuromodulation system.

FIG. 2 illustrates, by way of example, an embodiment of a neuromodulation system. The illustrated system 210 includes electrodes 211, a modulation device 212, and a programming system such as a programming device 213. The programming system may include multiple devices. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters. The modulation parameters may specify the electrical waveform (e.g. pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
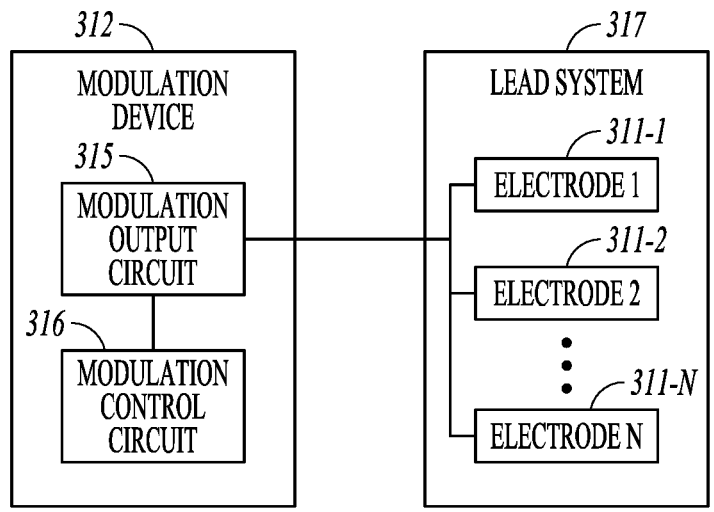
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers the neuromodulation. Neuromodulation pulses are provided herein as an example. However, the present subject matter is not limited to pulses, but may include other electrical waveforms (e.g. waveforms with different waveform shapes, and waveforms with various pulse patterns). The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes a paddle lead.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g. pulses), presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Figure 4:
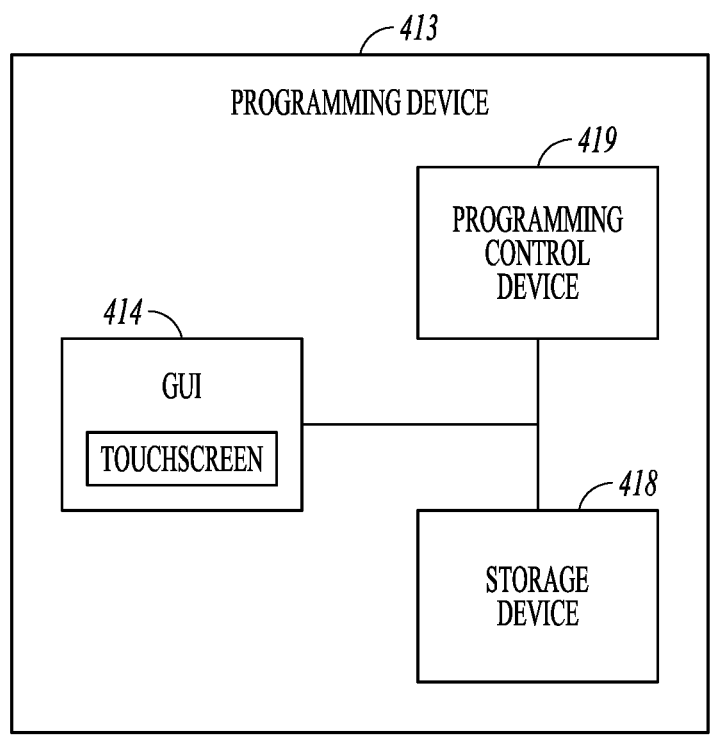
FIG. 4 illustrates, by way of example, an embodiment of a programming system such as a programming device, which may be implemented as the programming device in the neuromodulation system of FIG. 2.

FIG. 4 illustrates an embodiment of a programming system such as a programming device 413, which may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
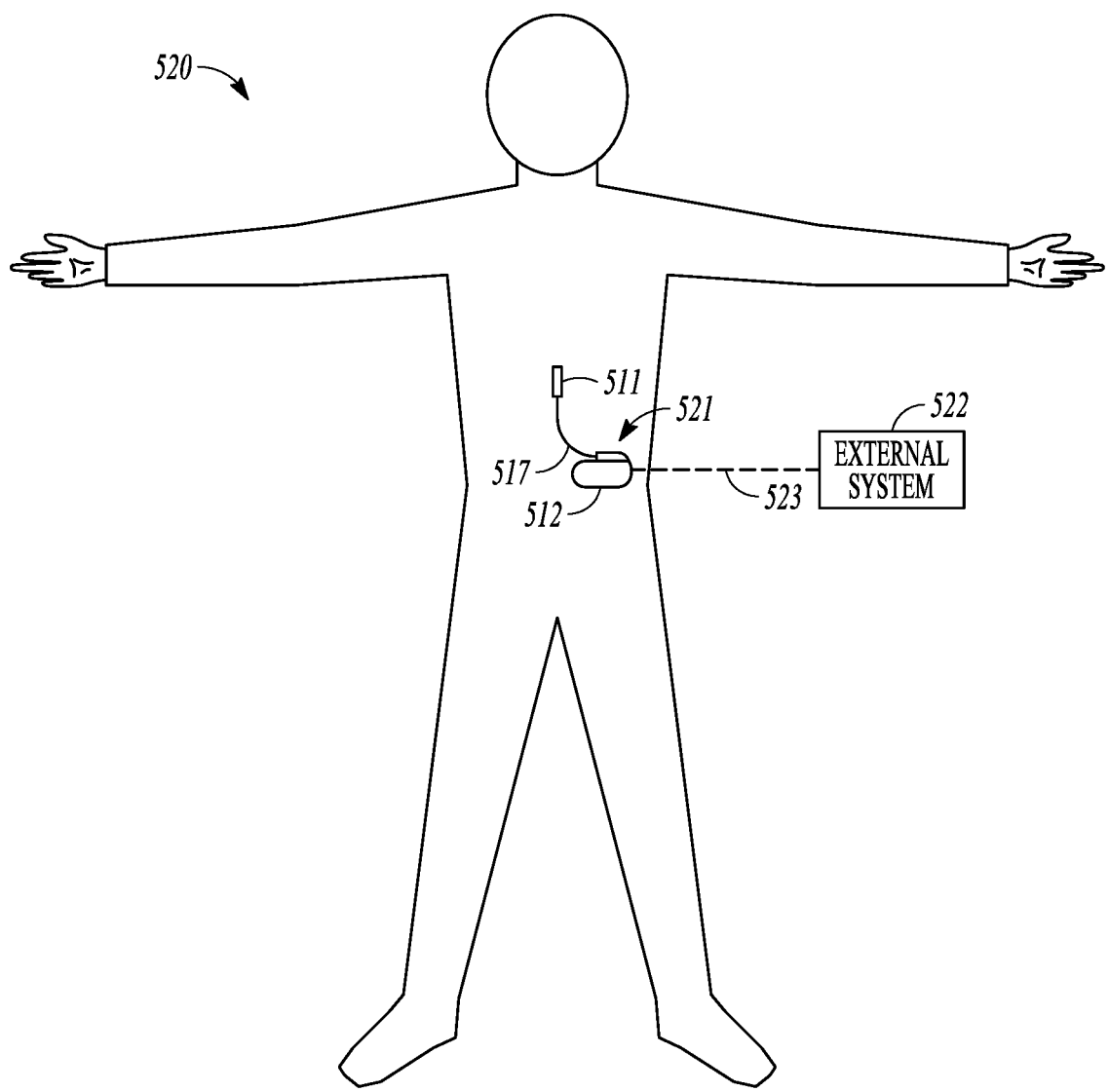
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 522 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

By way of example and not limitation, the neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s). Other embodiments may use other techniques to position electrodes operably near targeted tissue.

Figure 6:
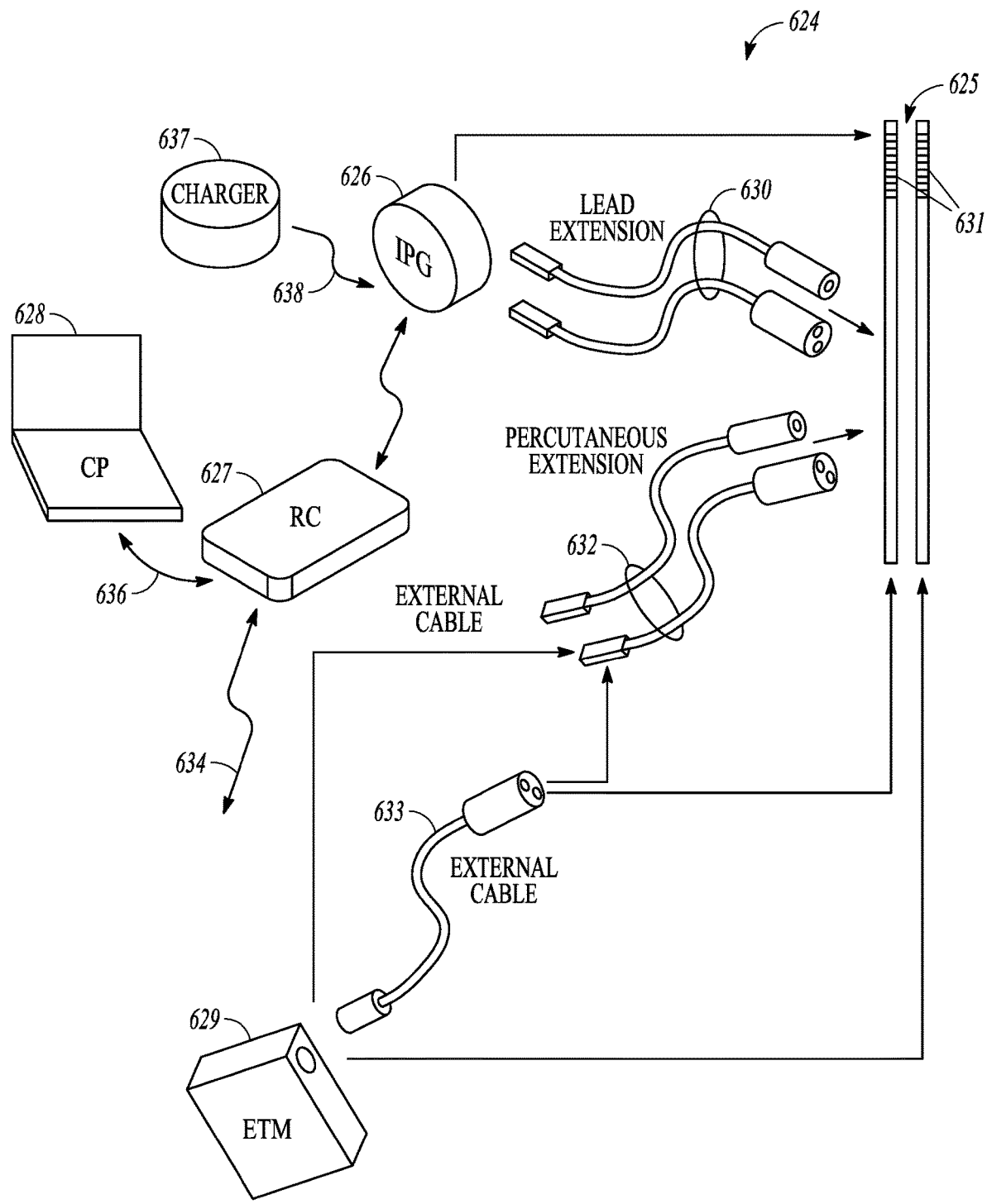
FIG. 6 illustrates, by way of example, an embodiment of a SCS system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an electrical waveform generator 626, an external remote controller RC 627, a clinician's programmer (CP) 628, and an external trial modulator (ETM) 629. IPGs are used herein as an example of the electrical waveform generator. However, it is expressly noted that the waveform generator may be configured to deliver repeating patterns of pulses, irregular patterns of pulses where pulses have differing amplitudes, pulse widths, pulse intervals, and bursts with differing number of pulses. It is also expressly noted that the waveform generator may be configured to deliver electrical waveforms other than pulses. The waveform generator 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the waveform generator case function as a case electrode) to allow for lateral steering of the current. Alternatively, a surgical paddle lead can be used in place of one or more of the percutaneous leads. In some embodiments, the waveform generator 626 may include pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar waveform generation circuitry as the waveform generator 626 to deliver electrical modulation energy to the electrodes accordance with a set of modulation parameters. The ETM 629 is a non-implantable device that is used on a trial basis after the neuromodulation leads 625 have been implanted and prior to implantation of the waveform generator 626, to test the responsiveness of the modulation that is to be provided. Functions described herein with respect to the waveform generator 626 can likewise be performed with respect to the ETM 629.

The RC 627 may be used to telemetrically control the ETM 629 via a bi-directional RF communications link 634. The RC 627 may be used to telemetrically control the waveform generator 626 via a bi-directional RF communications link 635. Such control allows the waveform generator 626 to be turned on or off and to be programmed with different modulation parameter sets. The waveform generator 626 may also be operated to modify the programmed modulation parameters to actively control the characteristics of the electrical modulation energy output by the waveform generator 626. A clinician may use the CP 628 to program modulation parameters into the waveform generator 626 and ETM 629 in the operating room and in follow-up sessions.

The CP 628 may indirectly communicate with the waveform generator 626 or ETM 629, through the RC 627, via an IR communications link 636 or other link. The CP 628 may directly communicate with the waveform generator 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, minicomputer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the waveform generator 626 to allow the desired parameters to be determined based on patient feedback or other feedback and for subsequently programming the waveform generator 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant waveform generator, implant waveform generator and lead(s), replace waveform generator, replace waveform generator and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the waveform generator via a wireless link such as an inductive link 638. Once the waveform generator has been programmed, and its power source has been charged by the external charger or otherwise replenished, the waveform generator may function as programmed without the RC or CP being present.

SCS, by way of example and not limitation, has been used to treat chronic pain syndromes. A change in posture of a patient receiving SCS may cause a change in thickness of cerebrospinal fluid between the one or more electrodes and the target site, which may impact effectiveness of the SCS or cause a patient to experience discomfort. The present subject matter relates to the use of sensed electrical activity, such as ESG, to make noise-sensitive patient-specific adjustments of stimulation parameters for SCS neuromodulation. Other types of sensed electrical activity may be used without departing from the scope of the present subject matter. For example, some embodiments can use a skin patch electrode to sense electrical activity. The following provides an overview of ESG.

ESG is a recording of electrical activity from the spinal cord. Many nerve cells produce low-level electrical signals, called action potentials, that form electrical activity patterns and, in many instances, can have an additive effect producing a magnified neural response. An example is the evoked compound action potential (ECAP), which is evoked by a stimulation such as a neurostimulation pulse and results from many neural cells firing simultaneously or close in time. An ESG signal also include neural components having a random appearance and representing activities of many different types of cells of the patient's nervous system that spontaneously fire over the time. The ESG signal further includes non-neural components representing various physical movements of the patient, such as movements associated with cardiac activities, respiratory activities, and skeletomuscular activities.

An ESG signal can be sensed non-invasively using surface electrodes attached to the patient's skin. This surface sensing usually requires an amplifier with high gain and high signal-to-noise ratio (SNR). An ESG signal can also be sensed invasively using electrodes incorporated onto one or more percutaneous or implantable leads. In one example, the ESG signal is sensed epidurally using epidural electrodes placed adjacent or over the dura, which is a membrane structure surrounding the spinal cord and the cerebral cortex of the patient. In another example, the ESG signal is sensed intradurally using a lead that penetrates the dura such that the electrodes can be placed subdurally within the spinal cord.

Findings from recent clinical studies suggest fast acting pain relief can be achieved by using SCS with active recharge waveforms with intensity just below the threshold for paresthesia resulting from dorsal column activation. ESG signals can be sensed from the patient to indicate characteristics (e.g., amplitude and shape) of the patient's dorsal column response to the stimulation, and therefore can be used for evaluation of stimulation parameters (e.g., waveforms and tissue sites of stimulation) to select a suitable pattern of stimulation. It has been observed that the neural responses evoked by SCS with active recharge waveforms exhibit an increasing magnitude and a changing shape as the stimulation increases and changes, respectively, with stimulation amplitude, stimulation pulse width, and/or closeness of stimulation site to the spinal cord. Dorsal column fibers of different diameters are known to produce a neural response after different delays, with fibers of smaller diameters associated with greater delays. The ECAP detectable from the ESG is a result of additive effect of the multiple action potentials produced by different axons of different diameters firing with different delays. The present system can use ESG to indicate a desirable response of neurostimulation to control delivery of a therapy to the patient.

Various components of an ESG signal can be sensed using the present subject matter, including but not limited to: the evoked neural response, the spontaneous neural response, the artifact activity (a deflection in the ESG signal caused by stimulation propagating through patient tissue), and noise present in a physiological sensed signal.

In this document, a "patient" includes a person receiving treatment delivered using a neurostimulation system according to the present subject matter, a "user" includes a physician or other caregiver who treats the patient using the neurostimulation system.

A change in posture of a patient receiving SCS may cause a change in thickness of cerebrospinal fluid between the one or more electrodes and the target site, which may impact effectiveness of the SCS due to inadequate stimulation delivery, or cause a patient to experience discomfort due to excessive stimulation delivery. In various embodiments, the present subject matter automatically adjusts stimulation in a closed-loop system based on sensed electrical activity, such as ESG-derived features, to minimize influence of noise and optimize system performance for a range of patient characteristics, including a posture or posture change of the patient. Some embodiments of the present subject matter use probabilistic modeling of features, dynamical systems modeling and/or a risk-sensitive control strategy, such as by using a programming device 413 and/or an IPG 512. In addition, various embodiments employ a strategic data collection procedure that minimizes clinical training time and computational resources required. Various embodiments utilize real-time operation on an IPG by embedding algorithms in hardware, firmware or a microprocessor unit of the IPG. Design parameters are selected for clinical use by using model-based simulations and clinical studies, in various embodiments. The present subject matter provides superior pain control outcomes with a model-based, responsive, closed-loop SCS system utilizing smart, predictive algorithms capable of anticipating patient needs.

In various embodiments, the present subject matter provides algorithms (such as by using a programming device 413 and/or an IPG 512) and methods to augment closed-loop SCS sensing-based approaches by using dynamic models of spinal cord motion to reduce the influence of noise on sensing and decision making. The present subject matter uses a set of algorithms, data collection and model training procedures to efficiently enable a patient to use the system for automatic intensity management to adjust SCS in real-time to compensate for changes in dorsal width of cerebrospinal fluid (dCSF) in response to postural changes, in various embodiments.

Figure 7:
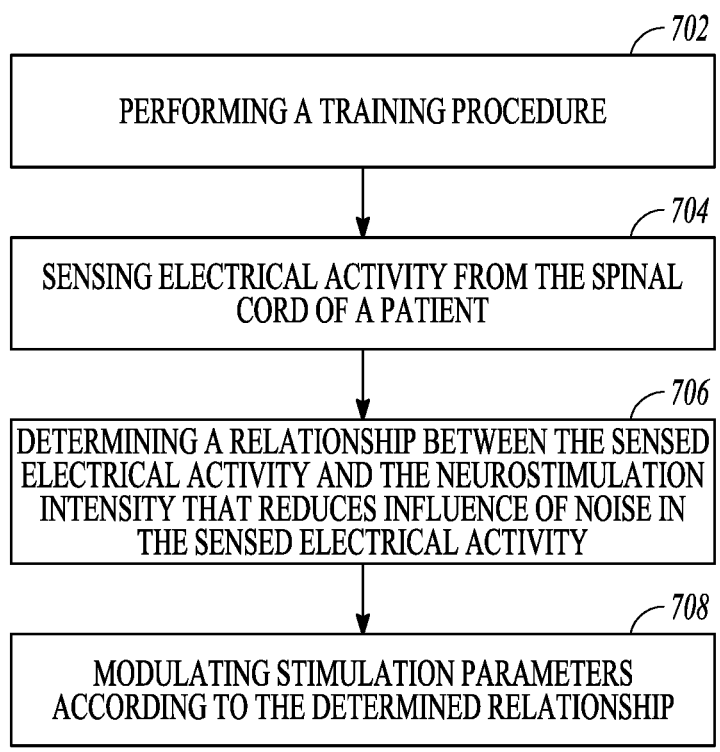
FIG. 7 illustrates, by way of example, an embodiment of a method for noise-sensitive patient-specific adjustments of stimulation parameters for neuromodulation.

FIG. 7 illustrates, by way of example, an embodiment of a method for noise-sensitive patient-specific adjustments of stimulation parameters for neuromodulation. The method may include performing a training data collection procedure, at step 702. At step 704, electrical activity is sensed from the spinal cord of a patient e. A relationship may be determined between the sensed electrical activity and the neurostimulation intensity that reduces influence of noise in the sensed electrical activity, at step 706. At step 708, stimulation parameters may be modulated according to the determined relationship. Various stimulation parameters can be modulated, including but not limited to: current amplitude, frequency, pulse width, stimulation fractionalization, and combinations thereof. Stimulation parameters may be modulated based on a perceived position or posture of a patient, in various embodiments. Posture of a patient may be inferred from the sensed electrical activity (such as ESG measurements) derived during training, in various embodiments. In other embodiments, posture of a patient may be sensed using an accelerometer, such as in a mobile device. In some embodiments, stimulation parameters may be modulated based on sensed lead migration.

In various embodiments, the method delivers neurostimulation energy through a plurality of electrodes to a patient having a spinal cord, and the method may include performing a training procedure by delivering the neurostimulation energy at one or more neurostimulation intensity levels to a neural target of the patient when the patient is at one or more postures or performing activities in which posture changes dynamically to evoke a response for each evaluated combination of neurostimulation intensity level and dynamically changing posture. An electrospinogram (ESG) may be received for each of the evaluated combinations, the ESG being a recording of electrical activity from the spinal cord, the electrical activity including the delivered neurostimulation energy and responses to the delivered neurostimulation energy, and extracting features from the ESG related to the delivered neurostimulation energy or evoked response for each of the evaluated combinations. A relationship may be determined between ESG features varying with dynamically changing postures of the patient and the intensity of the neurostimulation energy that reduces influence of noise in the received ESG using mathematical or statistical modeling of the extracted features for each of the evaluated combinations. Delivery of the neurostimulation energy may be controlled using the ESG according to the determined relationship by modulating stimulation parameters. Other types of electrical activity may be sensed without departing from the scope of the present subject matter.

The present subject matter determines a relationship between the sensed electrical activity and the neurostimulation intensity that reduces influence of noise in the sensed electrical activity. In one example, the relationship includes a determined relationship between ESG features varying with dynamically changing postures of the patient and the intensity of the neurostimulation energy that reduces influence of noise in the received ESG using mathematical or statistical modeling of the extracted features for each of the evaluated combinations. In various embodiments, the relationship is determined using a look-up table of parameters derived from the training procedure. In some embodiments, the relationship is based on features derived from the probabilistic and dynamical model. The probabilistic model may provide an estimate derived from the training procedure, while the dynamical model refines the estimate based on how the spinal cord of the patient is moving, including sequentially updating the data based on a series of calculations, in various embodiments. A trend is determined based on the sensed electrical activity to determine the posture using the training data, in some embodiments. Physical activity of the patient and time of day can be used as inputs, in various embodiments.

According to various embodiments, the mathematical modeling may include using a probabilistic model implementing a neural network or other statistical models. The probabilistic model may use a small amount of training data, such as two postures and stimulation energy levels, to obtain a modeled output, in various embodiments. The dynamical model may further reduce the influence of noise by modeling the dynamics of the spinal cord of the patient, using kinematics to track distance between electrodes and a target, in various embodiments. The mathematical modeling may include using a dynamical model incorporating one or more of a Kalman filter (KF) or a Hidden Markov Model (HMM), in various embodiments. The mathematical modeling may include using a risk-sensitive control strategy based on a selection of risk parameters specific for the patient, according to various embodiments. In some embodiments, the selection of risk parameters may include an indication of pain or discomfort tolerance of the patient. Various thresholds may be used for the selection of risk parameters, including but not limited to: perception threshold, therapeutic threshold, and discomfort threshold. The mathematical modeling may include using a probabilistic model implementing a neural network or other statistical models and a dynamical model incorporating one or more of a Kalman filter (KF) or a Hidden Markov Model (HMM), in an embodiment. In one embodiment, the mathematical modeling may include using a probabilistic model implementing a neural network or other statistical models and a risk-sensitive control strategy based on a selection of risk parameters specific for the patient. The mathematical modeling may include using a dynamical model incorporating one or more of a Kalman filter (KF) or a Hidden Markov Model (HMM) and a risk-sensitive control strategy based on a selection of risk parameters specific for the patient, in an embodiment. In some embodiments, the mathematical modeling may include using a probabilistic model implementing a neural network or other statistical model, a dynamical model incorporating one or more of a Kalman filter (KF) or a Hidden Markov Model (HMM), and a risk-sensitive control strategy based on a selection of risk parameters specific for the patient.

Figure 8:
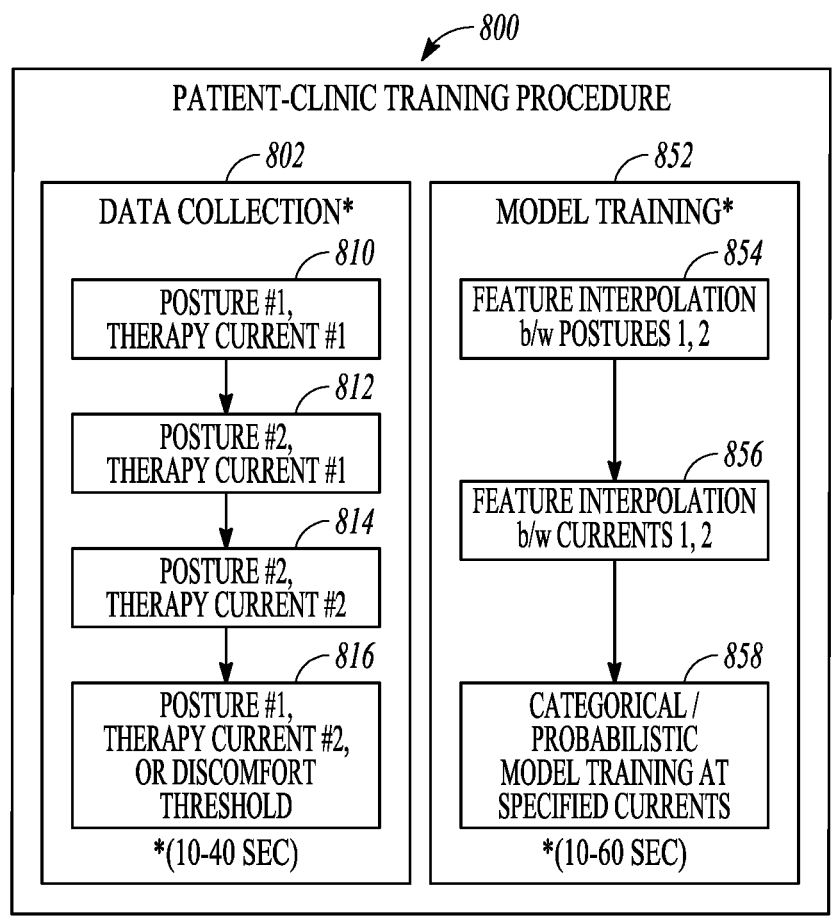
FIG. 8 illustrates, by way of example, an embodiment of a training procedure for noise-sensitive patient-specific adjustments of stimulation parameters for neuromodulation.

FIG. 8 illustrates, by way of example, an embodiment of a training procedure 800 for noise-sensitive patient-specific adjustments of stimulation parameters for neuromodulation. In a first portion of a patient-clinic training procedure 800, data collection 802 is performed at various patient postures and therapy current levels, in various embodiments. In one example, the data collection 802 may include collection of data at a first posture and a first therapy current 810, at a second posture and the first therapy current 812, at the second posture and a second therapy current 814, and at the first posture and the second therapy current or at a discomfort threshold 812. Data collection 802 may be performed over an interval of 10-40 seconds, in various embodiments. In a second portion of the patient-clinic training procedure 800, model training 852 may be performed by interpolation of data from data collection 802. At 854, model training 852 may include feature interpolation between the first posture and the second posture. The model training 852 may further include feature interpolation between the first therapy current and the second therapy current, at 856. The model training 852 may also include categorical and/or probabilistic model training at specified currents, at 858. Model training 852 may be performed over an interval of 10-60 seconds, in various embodiments.

Figure 9:
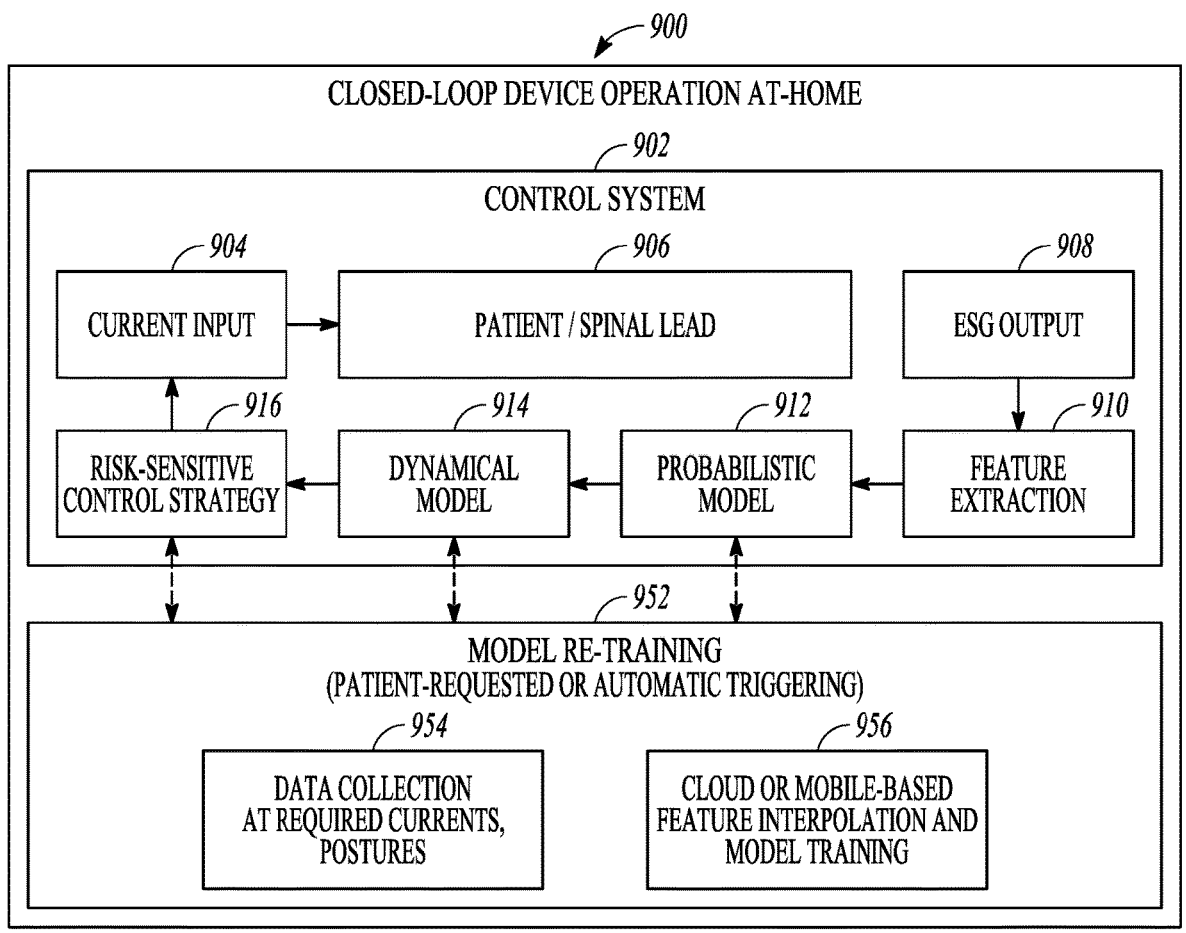
FIG. 9 illustrates, by way of example, an embodiment of a closed-loop procedure for noise-sensitive patient-specific adjustments of stimulation parameters for neuromodulation.

FIG. 9 illustrates, by way of example, an embodiment of a closed-loop procedure 900 for noise-sensitive patient-specific adjustments of stimulation parameters for neuromodulation. A control system 902, by way of example, may provide a current input 904 to a patient lead 906 for SCS neuromodulation, and senses the resulting electrical activity, such as ESG output 908. The control system 902 may extract features 910 from the ESG output 908, and may use one or more of a probabilistic model 912, a dynamical model 914, or a risk-sensitive control strategy 916 to train the system 902 to control the current input 904 for noise-sensitive patient-specific adjustments of stimulation parameters for neuromodulation, in various embodiments. Model re-training 952 may be provided, and different modes of re-training may be used in various embodiments, including automatically-triggered re-training (such as statistical testing) and/or manually requested re-training. By way of example, model re-training 952 may include further data collection 954 at predetermined currents and patient postures, and/or cloud or mobile-based feature interpolation and model training 956.

Figure 10A:
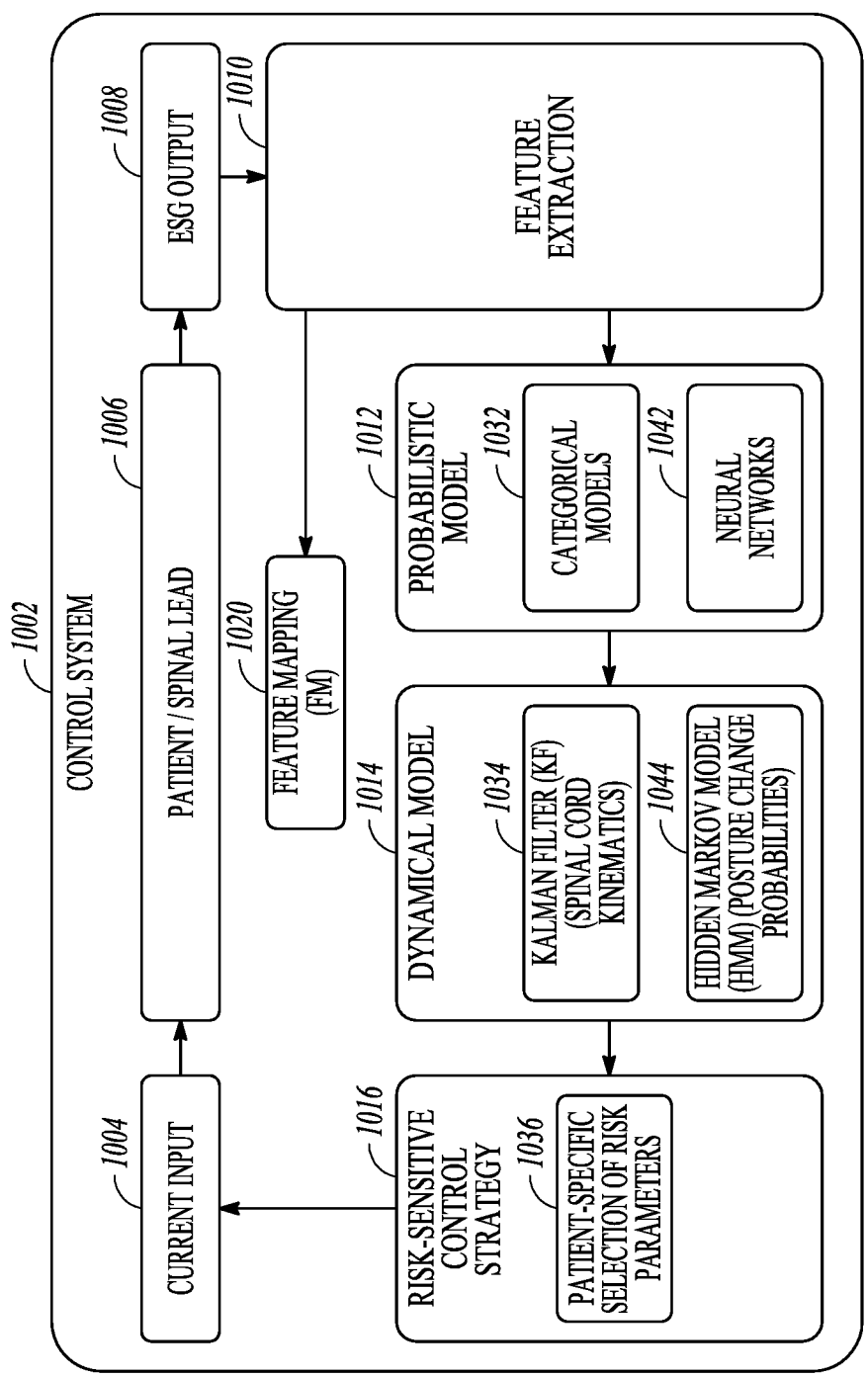
FIG. 10A illustrates, by way of example, an embodiment of a closed-loop system for noise-sensitive patient-specific adjustments of stimulation parameters for neuromodulation.

FIG. 10A illustrates, by way of example, an embodiment of a closed-loop system for noise-sensitive patient-specific adjustments of stimulation parameters for neuromodulation. A control system 1002, by way of example, may provide a current input 1004 to a patient lead 1006 for SCS neuromodulation, and may sense the resulting electrical activity, such as ESG output 1008. The control system 1002 may extract features 1010 from the ESG output 1008, and may use one or more of a probabilistic model 1012, a dynamical model 1014, or a risk-sensitive control strategy 1016 to train the system 1002 to control the current input 1004 for noise-sensitive patient-specific adjustments of stimulation parameters for neuromodulation, in various embodiments. In one example, the control system 1002 may include feature mapping (FM) 1020 of the extracted features. According to various embodiments, the probabilistic model 1012 may include one or more of categorical (such as statistical or mathematical) models 1032 and neural networks 1042. The dynamical model 1014 may include one or more of a Kalman Filter (KF) 1034 using spinal cord kinematics or a Hidden Markov Model (HMM) 1044 using posture change probabilities, in various embodiments. In various embodiments, the risk-sensitive control strategy 1016 may include patient-specific selection of risk parameters 1036.

Figure 10B:
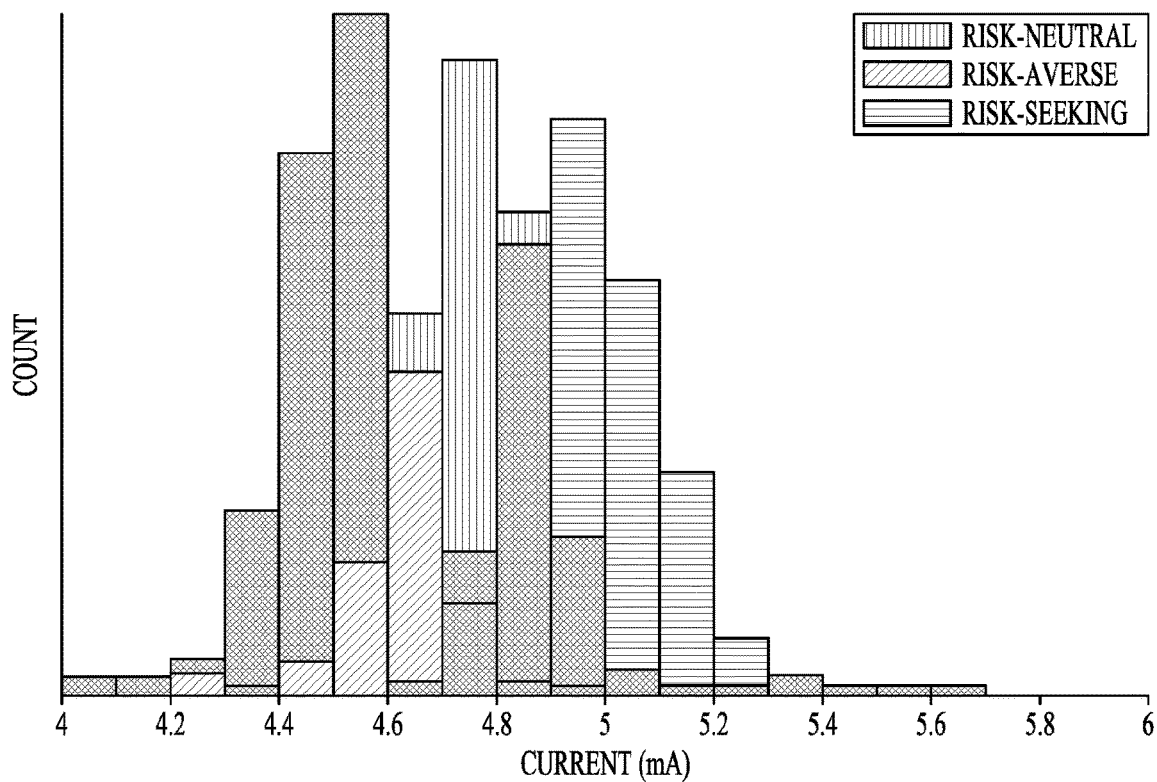
FIG. 10B-10C illustrate, by way of example, graphical outputs of embodiments for noise-sensitive patient-specific adjustments of stimulation parameters for neuromodulation.
Figure 10C:
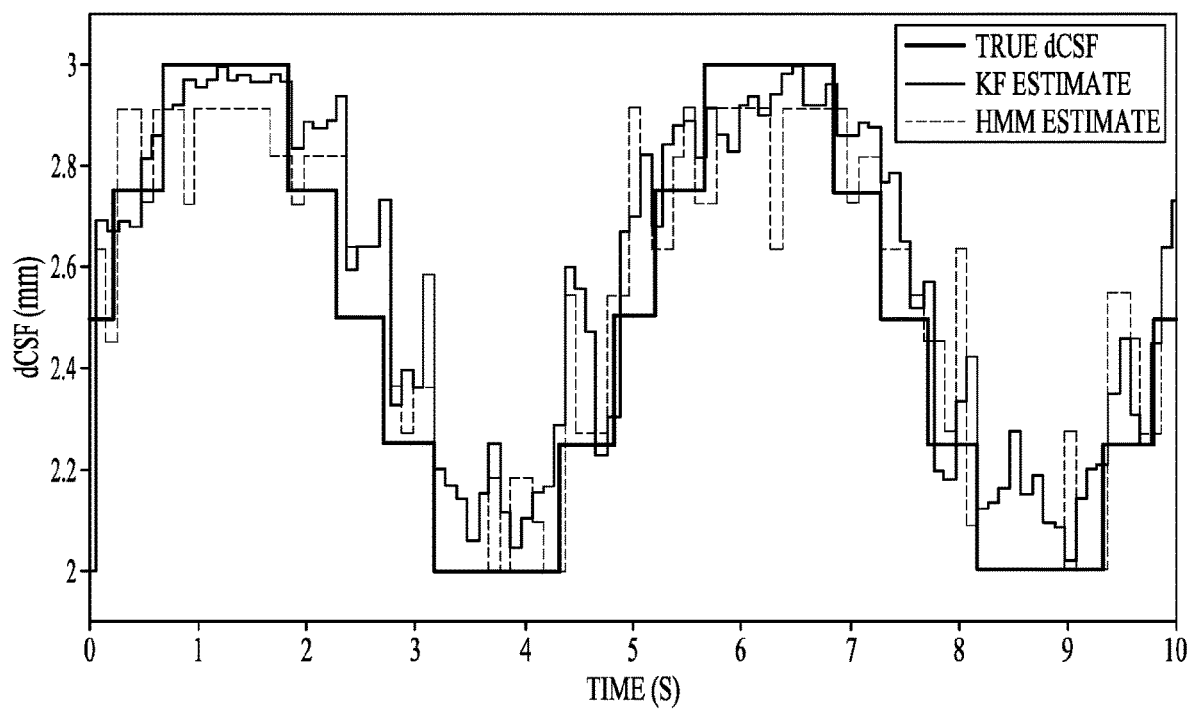

FIG. 10B-10C illustrate, by way of example, graphical outputs of embodiments for noise-sensitive patient-specific adjustments of stimulation parameters for neuromodulation. FIG. 10B illustrates a histogram illustrating risk levels for patient-specific selection of risk parameters. Various thresholds may be illustrated, including but not limited to perception thresholds, therapeutic thresholds, and discomfort thresholds. FIG. 10C illustrates a graph showing thickness of dCSF in a patient with dynamically changing posture using various models, including HMM, KF and probabilistic models, in various embodiments.

Figure 11:
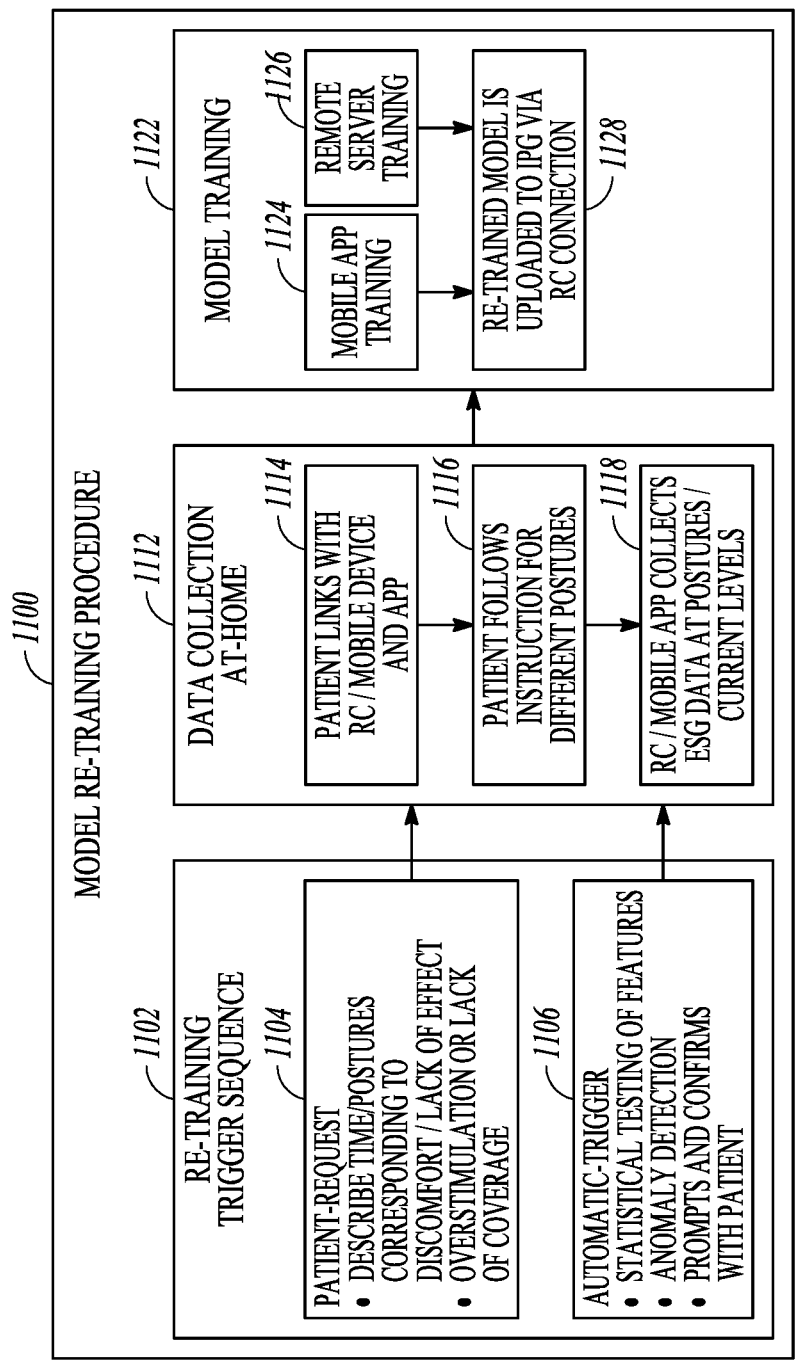
FIG. 11 illustrates, by way of example, an embodiment of re-training procedures for noise-sensitive patient-specific adjustments of stimulation parameters for neuromodulation.

FIG. 11 illustrates, by way of example, an embodiment of re-training procedures for noise-sensitive patient-specific adjustments of stimulation parameters for neuromodulation. The model re-training procedure 1100 may include a re-training trigger sequence 1102, and the re-training may be initiated based on a patient-request 1104 or an automatic trigger 1106. In various embodiments, the patient-request 1104 re-training sequence may be based on a description of time and postures corresponding to discomfort or lack of effect, and whether the applied SCS results in overstimulation or a lack of coverage of the stimulation. The automatic trigger 1106 re-training sequence may include statistical testing of features, anomaly detection, and prompts and confirms the re-training with the patient, in various embodiments. The model re-training procedure 1100 may further include at-home data collection 1112 in one example. The at-home data collection 1112 may begin with a patient link to a remote control (RC) or mobile device and application, at 1114. The patient may follow instructions from the RC or mobile device for different postures, at 1116. At 1118, the RC or mobile device may collect data from sensed electrical activity, such as ESG data, at the predetermined postures and current levels, in various embodiments. Model training 1122 based on the collected data may include mobile application training 1124 and remote server training 1126, in various embodiments, and the re-trained model may be uploaded to an IPG via a wireless connection to the RC or mobile device, at 1128.

Figure 12:
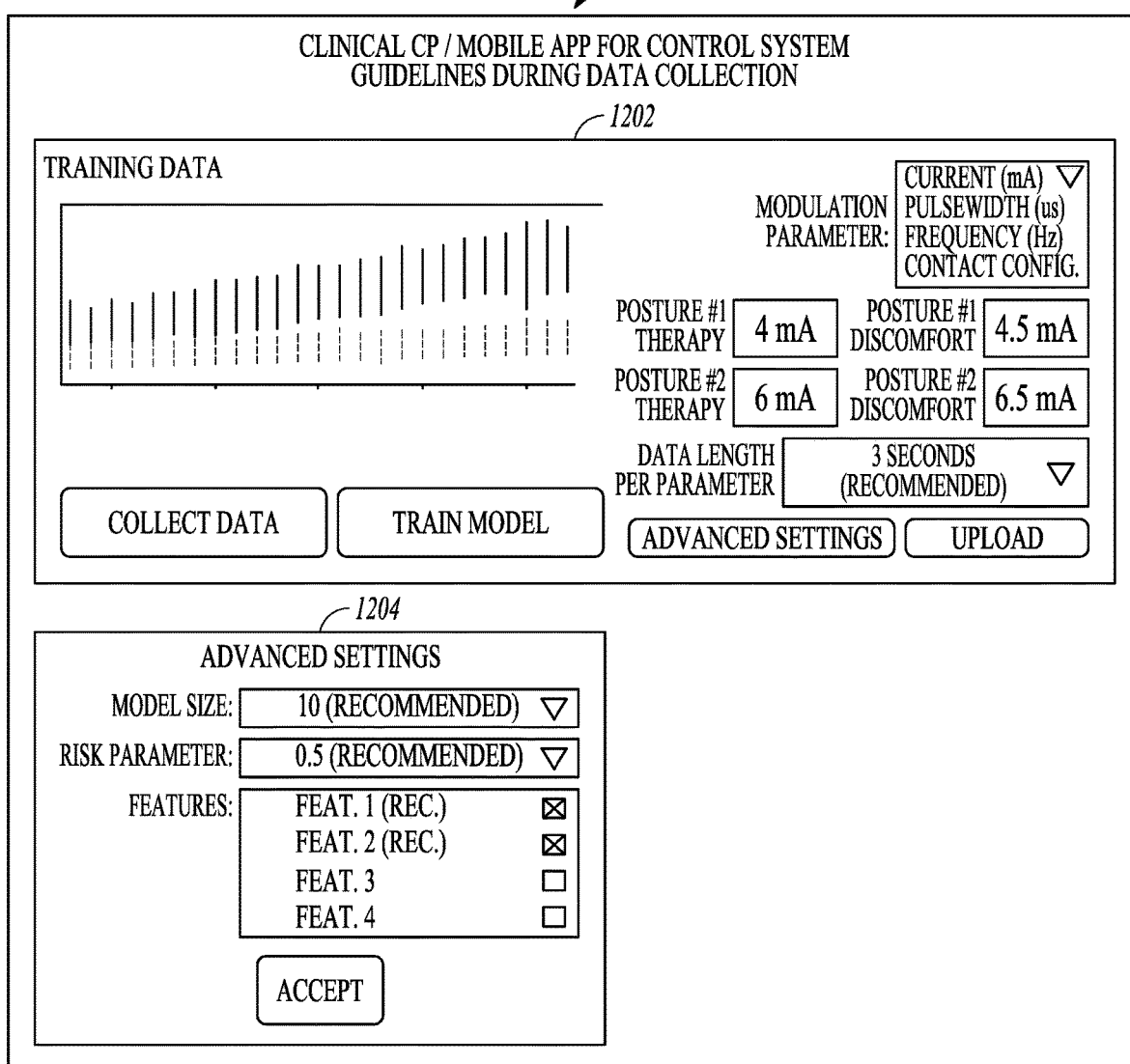
FIG. 12 illustrates, by way of example, an embodiment of an interface for noise-sensitive patient-specific adjustments of stimulation parameters for neuromodulation.

FIG. 12 illustrates, by way of example, an embodiment of an interface 1200 for noise-sensitive patient-specific adjustments of stimulation parameters for neuromodulation. In various embodiments, a clinical computer program or mobile application may provide the interface 1200 including a first portion 1202 for a user or a patient to collect and enter training data for various postures and inputs, and a second portion 1202 for advanced settings such as model size, risk parameters, and features. The interface 1200 may include data entry, parameter selection and various user-selectable portions to initiate data collection, model training, and data uploading, in various embodiments.

Figure 13A:
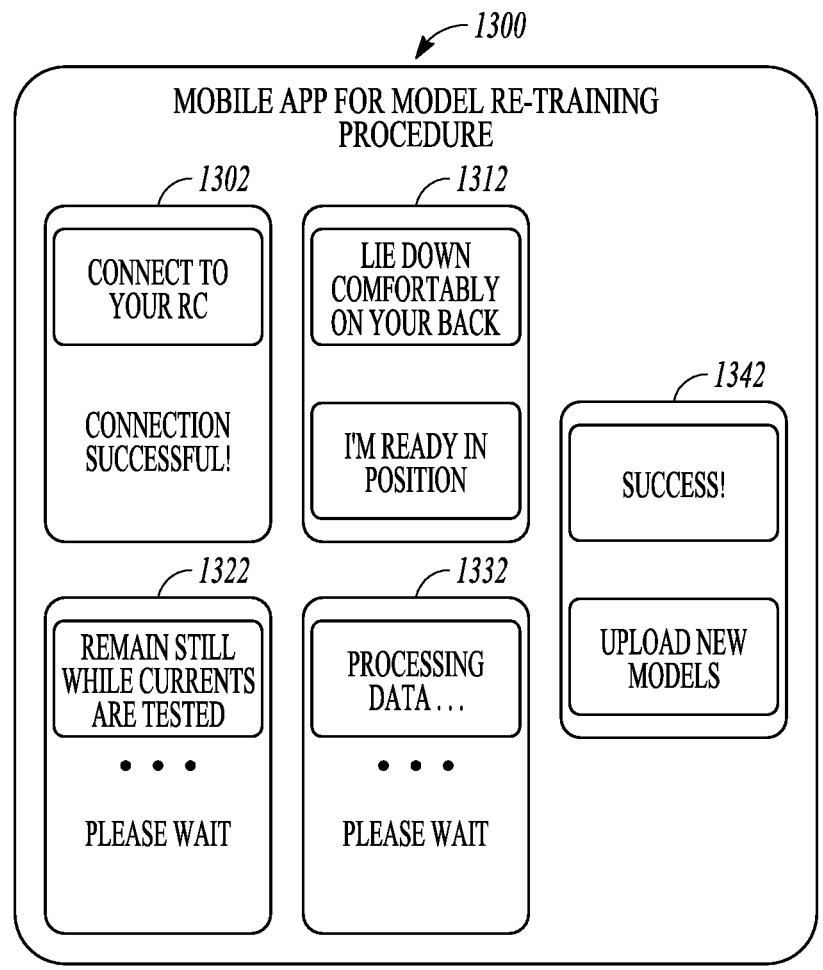
FIGS. 13A-13B illustrate, by way of example, embodiments of a mobile application for noise-sensitive patient-specific adjustments of stimulation parameters for neuromodulation.
Figure 13B:
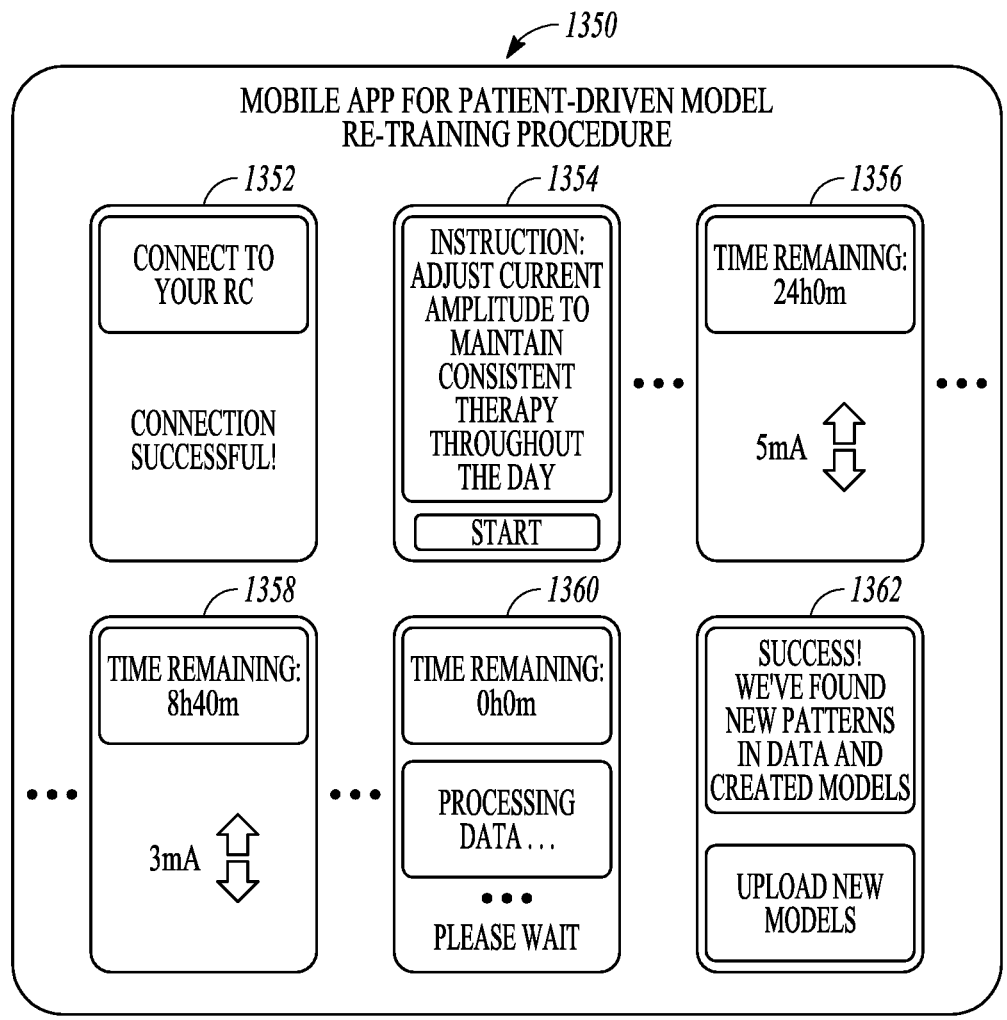

FIGS. 13A-13B illustrate, by way of example, embodiments of a mobile application 1300 for noise-sensitive patient-specific adjustments of stimulation parameters for neuromodulation. FIG. 13A illustrates an embodiment where the re-training procedure uses stimulation parameters identified by the training module or a clinician. In FIG. 13A, a mobile device GUI interface may include a first display 1302 that instructs a user or a patient to connect the IPG to a remote control (RC) and informs the patient when the connection is successful. A second display 1312 of the interface may instruct the patient to get in a specified position for data collection, and may provide an input for the patient to indicate when they are in the specified position. A third display 1322 of the interface may instruct the patient to remain in the specified position while predetermined currents are applied for neuromodulation, for example. A fourth display 1332 of the interface may inform the patient that data is being processed. A fifth display 1342 may provide the patient with an indication that data processing is completed, and may provide an input for the patient to upload new models to the IPG based on the re-training.

FIG. 13B illustrates an embodiment where the re-training procedure uses stimulation parameters provided by the patient using a remote control. In FIG. 13B, a mobile GUI interface includes a first display 1352 that instructs a user or a patient to connect the IPG to a remote control (RC) and informs the patient when the connection is successful. A second display 1354 of the interface may instruct the patient to adjust current amplitude to maintain constant therapy throughout the day. A third display 1356 and a fourth display 1358 may provide an interface for the patient to adjust the current input. A fifth display 1360 of the interface may inform the patient that data is being processed. A sixth display 1362 may provide the patient with an indication that data processing is completed, and may provide an input for the patient to upload new models to the IPG based on the re-training.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering neurostimulation energy through a plurality of electrodes to a patient having a spinal cord, the method comprising:
    performing a training procedure by delivering the neurostimulation energy at one or more neurostimulation intensity levels to a neural target of the patient when the patient is at a plurality of postures;
    sensing electrical activity from the spinal cord, the electrical activity including the delivered neurostimulation energy;
    extracting features from the sensed electrical activity when the patient is at the plurality of postures, including determining an influence of noise caused by dynamically changing posture of the patient;
    determining a relationship between the sensed electrical activity and neurostimulation intensity that reduces the influence of the noise in the sensed electrical activity caused by the dynamically changing posture of the patient using mathematical or statistical modeling of the extracted features; and
    modulating stimulation parameters according to the determined relationship.

2. The method of claim 1, wherein sensing the electrical activity includes using an electrospinogram (ESG).

3. The method of claim 1, wherein the mathematical modeling includes using a dynamical model incorporating one or more of a Kalman filter (KF) or a Hidden Markov Model (HMM).

4. The method of claim 1, wherein the mathematical modeling includes using a risk-sensitive control strategy based on a selection of risk parameters specific for the patient.

5. The method of claim 4, wherein the selection of risk parameters includes an indication of pain or discomfort tolerance of the patient.

6. The method of claim 1, wherein the mathematical modeling includes using a probabilistic model implementing a neural network and a dynamical model incorporating one or more of a Kalman filter (KF) or a Hidden Markov Model (HMM).

7. The method of claim 1, wherein the mathematical modeling includes using a probabilistic model implementing a neural network and a risk-sensitive control strategy based on a selection of risk parameters specific for the patient.

8. The method of claim 1, wherein the mathematical modeling includes using a dynamical model incorporating one or more of a Kalman filter (KF) or a Hidden Markov Model (HMM) and a risk-sensitive control strategy based on a selection of risk parameters specific for the patient.

9. The method of claim 1, wherein the mathematical modeling includes using a probabilistic model implementing a neural network, a dynamical model incorporating one or more of a Kalman filter (KF) or a Hidden Markov Model (HMM), and a risk-sensitive control strategy based on a selection of risk parameters specific for the patient.

10. The method of claim 9, wherein the selection of risk parameters includes an indication of a discomfort threshold of the patient.

11. A non-transitory machine-readable medium including instructions, which when executed by a machine, cause the machine to perform a method for delivering neurostimulation energy through a plurality of electrodes to a patient having a spinal cord, the method comprises:
   performing a training procedure by delivering the neurostimulation energy at one or more neurostimulation intensity levels to a neural target of the patient when the patient is at a plurality of postures;
   sensing electrical activity from the spinal cord, the electrical activity including the delivered neurostimulation energy;
   extracting features from the sensed electrical activity when the patient is at the plurality of postures, including determining an influence of noise caused by dynamically changing posture of the patient;
   determining a relationship between the sensed electrical activity and neurostimulation intensity that reduces the influence of the noise in the sensed electrical activity caused by the dynamically changing posture of the patient using mathematical or statistical modeling of the extracted features; and
   modulating stimulation parameters according to the determined relationship.

12. The machine-readable medium of claim 11, wherein sensing the electrical activity includes using an electrospinogram (ESG).

13. The machine-readable medium of claim 11, wherein the one or more neurostimulation intensity levels includes a discomfort threshold of the patient.

14. The machine-readable medium of claim 11, wherein the one or more neurostimulation intensity levels includes a perception threshold of the patient.

15. The machine-readable medium of claim 11, wherein the one or more neurostimulation intensity levels includes a therapeutic threshold of the patient.

16. A system for delivering neurostimulation energy through a plurality of electrodes, comprising:
   an implantable pulse generator (IPG) configured for spinal neurostimulation therapy;
   one or more leads configured to connect the IPG to the plurality of electrodes;
   a stimulation control circuit configured to deliver the neurostimulation energy using the plurality of electrodes at one or more neurostimulation intensity levels to a neural target at or near a spinal cord of a patient when the patient is at a plurality of postures;
   a sensing input configured to sense electrical activity from the spinal cord, the electrical activity including responses to the delivered neurostimulation energy;
   a feature extraction module configured to extract features from the sensed electrical activity when the patient is at the plurality of postures, including determining an influence of noise caused by dynamically changing posture of the patient; and
   a training module configured to determine a relationship between the sensed electrical activity and neurostimulation intensity that reduces the influence of the noise in the sensed electrical activity caused by the dynamically changing posture of the patient using mathematical or statistical modeling of the extracted features;
   wherein the stimulation control circuit is further configured to modulate stimulation parameters according to the determined relationship.

17. The system of claim 16, wherein the sensing input is configured to receive an electrospinogram (ESG).

18. The system of claim 16, wherein the mathematical modeling includes using a dynamical model incorporating one or more of a Kalman filter (KF) or a Hidden Markov Model (HMM).

19. The system of claim 16, wherein the mathematical modeling includes using a risk-sensitive control strategy based on a selection of risk parameters specific for the patient.

20. The system of claim 19, wherein the selection of risk parameters includes an indication of pain or discomfort tolerance of the patient.

* * * * *